United States Patent [19]

Marhold et al.

[11] Patent Number: 4,792,635

[45] Date of Patent: Dec. 20, 1988

[54] SYMMETRIC BENZOPHENONES SUBSTITUTED BY GROUPS CONTAINING FLUORINE

[75] Inventors: Albrecht Marhold, Leverkusen; Erich Klauke, Odenthal; Ernst Kysela, Bergisch-Gladbach, all of Fed. Rep. of Germany

[73] Assignee: Bayer Aktiengesellschaft, Leverkusen, Fed. Rep. of Germany

[21] Appl. No.: 713,513

[22] Filed: Mar. 19, 1985

[30] Foreign Application Priority Data

Mar. 28, 1984 [DE] Fed. Rep. of Germany ....... 3411326

[51] Int. Cl.$^4$ .............................................. C07C 49/80
[52] U.S. Cl. .................... 568/332; 549/362; 549/435; 568/333
[58] Field of Search ............... 568/316, 332, 333; 549/362, 435

[56] References Cited

U.S. PATENT DOCUMENTS

| | | | |
|---|---|---|---|
| 2,806,059 | 9/1957 | Bruson et al. | 568/332 |
| 3,106,587 | 10/1963 | Harms | 568/332 |
| 3,326,928 | 6/1967 | Mattson | 568/332 |
| 3,455,985 | 7/1969 | Sternbach et al. | 568/332 |
| 3,465,051 | 9/1969 | Pecherer | 71/105 |
| 3,732,307 | 5/1973 | Middleton | 71/78 |
| 4,027,040 | 5/1977 | Deraedt et al. | 568/332 |
| 4,120,687 | 10/1978 | Meisinger | 71/78 |

FOREIGN PATENT DOCUMENTS

| | | | |
|---|---|---|---|
| 0004710 | 10/1979 | European Pat. Off. | |
| 0101760 | 3/1984 | European Pat. Off. | 568/316 |
| 0156278 | 10/1985 | European Pat. Off. | 568/332 |
| 3151365 | 7/1983 | Fed. Rep. of Germany | |
| 446450 | 4/1936 | United Kingdom | |
| 907828 | 10/1962 | United Kingdom | 568/332 |

OTHER PUBLICATIONS

Chemical Abstracts, Band 80, 1974, Seite 85, Nr. 134887e, Columbus, Ohio, US; M. I. Dronkina et al.: "Triphenylmethane Dyes Containing bis(trifluoromethyl)amino Groups" & ZH. ORG. KHIM. 1973, 9(10), 2167–72.

Chemistry Letters, Nr. 6, Jun. 1984, Seiten 881–884, The Chemical Society of Japan; K. Takuma et al.: "An Effect of Trifluoromethyl Group on Photosensitizing Behavior of Benzophenone Derivatives" *Seite 881*.

Bull. Soc. Chim. France, 1962, 587–593, J. Lichtenberger & F. Weiss.

*Primary Examiner*—Nicky Chan
*Attorney, Agent, or Firm*—Sprung Horn Kramer & Woods

[57] ABSTRACT

Symmetric benzophenones substituted by groups containing fluorine are prepared by reacting aromatic compounds substituted by groups containing fluorine with formaldehyde and/or a formaldehyde derivative, with the addition of hydrogen fluoride, fluorosulphonic acid and/or sulphuric acid, to give the corresponding diphenylmethanes and oxidizing these. The symmetric benzophenones substituted by groups containing fluorine are used for the preparation of polyether ketones by reacting them with diols. New symmetric benzophenones substituted by groups containing fluorine are also disclosed.

2 Claims, No Drawings

SYMMETRIC BENZOPHENONES SUBSTITUTED BY GROUPS CONTAINING FLUORINE

The present invention relates to a process for the preparation of symmetric benzophenones substituted by groups containing fluorine by reaction of aromatic compounds substituted by groups containing fluorine with formaldehyde and/or a formaldehyde derivative, with the addition of hydrogen fluoride, fluorosulphonic acid and/or sulphuric acid, to give symmetric diphenylmethanes substituted by groups containing fluorine, and oxidation thereof, and to the use of such benzophenones for the preparation of polyether ketones, and new symmetric benzophenones substituted by groups containing fluorine.

It has been reported that the reaction of aromatic compounds, for example benzotrifluoride, with paraformaldehyde and chlorosulphonic acid leads to the corresponding chloromethylated aromatic compounds, for example to 3-trifluoromethylbenzyl chloride (see U.S. Pat. No. 3,465,051). No condensation of two molecules of the aromatic starting compound to give the corresponding diphenylmethanes has been observed here.

The preparation of some diphenylmethanes substituted by groups containing fluorine from aromatic compounds substituted by groups containing fluorine and alkylating agents substituted by groups containing fluorine in the presence of hydrogen fluoride, for example the preparation of bis-(3-trifluoromethyl-phenyl)methane from trifluoromethyl-benzyl methyl ether and benzotrifluoride, is described in German Offenlegungsschrift No. 3,151,365. This process has the disadvantage that two differently substituted aromatic starting compounds must be used, even for the preparation of symmetric diphenyl methanes substituted by groups containing fluorine.

Of the group of symmetric benzophenones substituted by groups containing fluorine, only one compound is yet known, that is to say 3,3'-bistrifluoromethylbenzophenone, which has been obtained from m-trifluoro-methyl-phenyl-magnesium bromide by reaction with m-trifluoromethyl-benzonitrile (see Bull. Soc. Chim. France 1962, 587-93). In this case also, two differently substituted aromatic starting compounds are to be employed for the preparation of the symmetric 3,3'-bistrifluoromethylbenzophenone. Furthermore, the Grignard reaction to be carried out here is unsuitable for industrial preparation. In respect of the usefulness of the 3,3'-bistrifluoromethyl-benzophenone, it is known from the same literature reference that 3,3'-bistrifluoromethyl-benzhydrol, 3-trifluoromethyl-benzhydrol and 3,3',3'',3'''-tetrakis-trifluoromethyl-benzopinacol can be prepared therefrom. A process has now been found for the preparation of symmetric benzophenones substituted by groups containing fluorine, of the formula

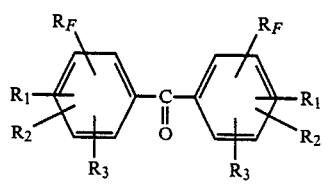

in which $R_F$ represents $CF_3$, $CF_2CF_3$, $CF_2CCl_3$, $OCF_3$, $OCF_2Cl$, $OCF_2CF_2H$, $OCF_2CHFCl$, $OCF_2CCl_3$, $SCF_3$, $SCF_2Cl$, $SCF_2CF_3$, $SCF_2CF_2H$, $SCF_2CHFCl$ or $N(CF_3)_2$ and $R_1$ represents hydrogen, or $R_F$ and $R_1$ together represent $-OCF_2O-$, $-OCF_2CF_2O-$, $-OCF_2CHFO-$ or $-OCF_2CFClO-$, and $R_2$ represents hydrogen, halogen, an alkyl, alkoxy or alkylthio group or an alkoxy or alkylthio group which is substituted by halogen, and $R_3$ represents hydrogen, halogen or an alkyl group, which is characterized in that aromatic compounds substituted by groups containing fluorine, of the formula

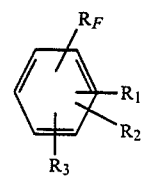

in which $R_F$, $R_1$, $R_2$ and $R_3$ have the abovementioned meaning, are reacted with formaldehyde and/or a formaldehyde derivative with the addition of hydrogen fluoride, fluorosulphonic acid and/or sulphuric acid, to give symmetric diphenylmethanes substituted by groups containing fluorine, of the formula

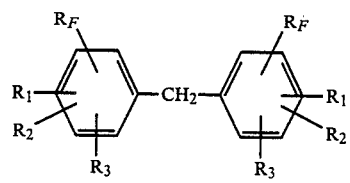

in which ($R_F$, $R_1$, $R_2$ and $R_3$ have the abovementioned meaning and these diphenylmethanes are oxidized.

If $R_2$ and/or $R_3$ in the formulae (I), (II) and (III) represents halogen or an alkoxy or alkylthio group which is substituted by halogen, halogen preferably represents fluorine and/or chlorine. If $R_2$ and/or $R_3$ in the formulae (I), (II) and (III) represents an alkyl, alkoxy or alkylthio group or an alkoxy or alkylthio group which is substituted by halogen, these groups preferably contain 1 to 6 and particular preferably 1 to 4 C atoms.

The aromatic compounds of the formulae (II) to be employed in the process according to the invention can be obtained, for example, in accordance with European published application No. 0,008,453, in accordance with European published application No. 0,011,179 or in accordance with J. Org. Chem. 44, 2,907 (1979) or in a manner analogous thereto.

Compounds of the formula (II) which are preferably employed in the process according to the invention are those in which $R_F$ represents $CF_3$, $OCF_3$, $OCF_2Cl$ or $SCF_3$ and $R_1$ represents hydrogen, or $R_F$ and $R_1$ together represent $-OCF_2CFClO-$, $-OCF_2O-$ or $-OCF_2CHFO-$, $R_2$ represents hydrogen, fluorine, chlorine or $C_1$- to $C_4$-alkyl and $R_3$ represents hydrogen or chlorine.

Benzotrifluoride, chlorobenzotrifluorides, fluorobenzotrifluorides, 2-chloro-5-methylbenzotrifluoride, trifluoromethoxybenzene, difluorochloromethoxybenzene, 2,2-difluorobenzodioxole, 2-chloro-2,3,3-trifluorobenzodioxene and 2,3,3-trifluorobenzodioxene are particularly preferably employed in the process according to the invention.

Formaldehyde can be employed, for example, in gaseous form, in the form of an oligomer (for example as trioxane) and/or in the form of a polymer (for example as polyoxymethylene). Examples of possible formaldehyde derivatives are halogenomethyl aryl ethers, halogenomethyl aryl thioethers, chloromethyl isocyanate, urotropine (=hexamethylenetetramine), methoxymethyl isocyanate and analogous compounds. Formaldehyde in a particular form and formaldehyde derivatives can in each case be employed by themselves or in any desired mixtures with one another. The use of trioxane and polyoxymethylene is preferred.

Formaldehyde and/or formaldehyde derivatives are in general employed in at least the stoichiometrically required amount. It is preferable to employ an excess of formaldehyde and/or formaldehyde derivatives, for example a 0.3- to 3-fold molar excess.

A condensing agent consisting of hydrogen fluoride, fluorosulphonic acid and/or sulphuric acid can be added in various amounts. For example, condensing agent amounts of 30 to 250% by weight, based on the compound of the formula (II) employed, are suitable. The amount of condensing agent is preferably 50 to 200% by weight, based on the compound of the formula (II) employed.

Hydrogen fluoride and fluorosulphonic acid are the preferred condensing agents.

The sequence in which the aromatic compound of the formula (II), formaldehyde and/or formaldehyde derivatives and condensing agent are brought together is of no significance.

The condensation reaction according to the invention can in general be carried out under normal pressure and at temperatures from, for example, 0 to 100° C. In particular, if hydrogen fluoride is employed as the condensing agent and temperatures above 20° C. are to be applied, it can also be carried out under pressure.

The condensation reaction according to the invention is preferably carried out only up to a conversion of 50 to 70%, based on the compound of the formula (II) employed.

The reaction mixture from the condensation reaction according to the invention can be worked up, for example, by discharging the reaction mixture onto ice-water, separating off the organic phase which forms or the solid organic product which forms and subjecting this to fractional distillation, preferably in vacuo, or recrystallizing it, for example from cyclohexane or methanol. After the reaction mixture has been discharged onto ice or water, it is also possible to take up the organic constituents in a solvent, for example in methylene chloride, and to isolate the product of the formula (III) from this solution, if necessary after washing and drying the solution. If hydrogen fluoride has been used as the condensing agent, a procedure can also be followed in which the hydrogen fluoride is removed by distillation under normal pressure and/or reduced pressure and the mixture which remains is subjected to fractional distillation, preferably in vacuo. The unreacted portions of the aromatic compounds of the formula (II) which are separated off, if appropriate, during working up can be reused in the process according to the invention.

It is not absolutely necessary to isolate and/or purify the products of the formula (III), but compounds of the formula (III) with the maximum possible purity are preferably employed in the subsequent oxidation reaction.

The diphenylmethane derivates of the formula (III) obtained in the manner described above are then oxidized. This oxidation can be carried out in a manner which is known per se. Examples of suitable oxidizing agents are nitric acid, chromic acid, chromates, dichromates, potassium permanganate, manganese dioxide, oxygen, air, selenium dioxide and peroxides, such as hydrogen peroxide and nickel peroxide. Preferred oxidizing agents are nitric acid, oxygen and chromium compounds in which the chromium is present in the oxidation level of +6. The oxidation is preferably carried out in an acid medium at elevated temperature.

The reaction products from this oxidation, i.e. the symmetric benzophenones substituted with groups containing fluorine, of the formula (I), can be isolated, for example by discharging the reaction mixture onto water or ice water and extracting it with an extraction agent, for example methylene chloride, and stripping off the extraction agent from the extract. If nitric acid is used as the oxidizing agent, a procedure can also be followed in which the reaction mixture is cooled and the solid constituents then present are separated off by filtration or centrifugation. If appropriate, the benzophenones of the formula (I) thus obtained can be further purified, for example by recrystallization, for example from methanol.

Symmetric benzophenones substituted by groups containing fluorine, of the formula (I), are rendered accessible in a simple manner which is also suitable for carrying out on an industrial scale by the process according to the invention. In view of the prior art described above, it is decidedly surprising that symmetric diphenylmethanes substituted by groups containing fluorine, of the formula (III), can be obtained by the condensation reaction according to the invention. In addition, it was to be expected that the water formed in the condensation reaction leads to the detachment of the fluorine-containing groups in the acid environment present. Only this good and easy accessibility of these diphenylmethanes makes it possible to prepare the benzophenones of the formula (I) therefrom.

The benzophenones of the formula (I) can be used, for example, for the preparation of novel polymers of the polyether ketone type.

The present invention furthermore relates to new symmetric benzophenones substituted by groups containing fluorine, of the formula

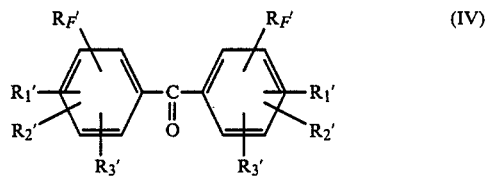

in which $R_F'$ represents $CF_3$, $CF_2CF_3$, $CF_2CCl_3$, $OCF_3$, $OCF_2Cl$, $OCF_2CF_2H$, $OCF_2CHFCl$, $OCF_2CCl_3$, $SCF_3$, $SCF_2Cl$, $SCF_2CF_3$, $SCF_2CF_2H$, $SCF_2CHFCl$ or $N(CF_3)_2$ and $R_1'$ represents hydrogen, or $R_F'$ and $R_1'$ together represent —$OCF_2O$—, —$OCF_2CF_2O$—, —$OCF_2CHFO$— or —$OCF_2CFClO$—, and $R_2'$ represents hydrogen, halogen, an alkyl, alkoxy or alkylthio group or an alkoxy or alkylthio group which is substituted by halogen, and $R_3'$ represents hydrogen, halogen or an alkyl group, with the exception of the compound in which $R_F'$ represents $CF_3$ in the 3- and 3'-position and $R_1'$, $R_2'$ and $R_3'$ represent hydrogen.

If $R_2'$ and/or $R_3'$ in formula (IV) represents halogen or an alkoxy or alkylthio group which is substituted by halogen, halogen preferably represents fluorine and/or chlorine.

If $R_2'$ and/or $R_3'$ in formula (IV) represents an alkyl, alkoxy or alkylthio group or an alkoxy or alkylthio group which is substituted by halogen, these groups preferably contain 1 to 6 and particularly preferably 1 to 4 C atoms.

Preferred compounds of the formula (IV) are those in which $R_F'$ represents $CF_3$, $OCF_3$, $OCF_2CL$ or $SCF_3$ and $R_1'$ represents hydrogen, or $R_F'$ and $R_1'$ together represent —$OCF_2O$—, —$OCF_2CF_2O$—, $OCF_2CH$-$FO$— or —$OCF_2CFClO$—, and $R_2'$ represents hydrogen, fluorine, chlorine or methyl and $R_3'$ represents hydrogen, fluorine, chlorine or methyl, with the exception of the compound in which $R_F'$ represents $CF_3$ in the 3- and 3'-position and $R_1'$, $R_2'$ and $R_3'$ represent hydrogen.

A particularly preferred compound of the formula (IV) is 4,4'-difluoro-3,3'-bistrifluoromethyl-benzophenone.

The present invention furthermore relates to the use of symmetric benzophenones substituted by groups containing fluorine, of the formula

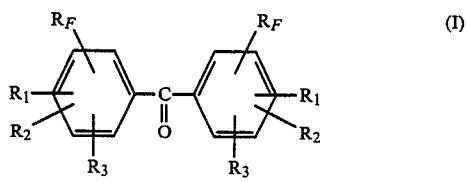

in which RF represents $CF_3$, $CF_2CF_3$, $CF_2CCl_3$, $OCF_3$, $OCF_2Cl$, $OCF_2CF_2H$, $OCF_2CHFCl$, $OCF_2CCl_3$, $SCF_3$, $SCF_2Cl$, $SCF_2CF_3$, $SCF_2CF_2H$, $SCF_2CHFCl$ or $N(CF_3)_2$ and $R_1$ represents hydrogen, or $R_F$ and $R_1$ together represent —$OCF_2O$—, —$OCF_2CF_2O$—, —$OCF_2CHFO$— or —$OCF_2CFClO$—, and $R_2$ represents hydrogen, halogen, an alkyl, alkoxy or alkylthio group or an alkoxy or alkylthio group which is substituted by halogen, and $R_3$ represents hydrogen, halogen or an alkyl group, for the preparation of polyether ketones by reaction with diols.

Compounds of the formula (I) in which RF represents $CF_3$, $R_1$ represents hydrogen, $R_2$ represents fluorine or chlorine and $R_3$ represents hydrogen are preferred for this use.

The diols are preferably aromatic diols, especially para substituted bisphenols. Examples of possible diols are hydroquinone, 4,4'-dihydroxydiphenyl ether, 4,4'-dihydroxydiphenyl sulphone and 4,4'-dihydroxybenzophenone. Hydroquinone is preferred.

The reaction of compounds of the formula (I) with diols is preferably carried out with the addition of alkalis, for examples alkali metal hydroxides or alkali metal hydrides, and in the presence of a polar solvent, such as N-methylpyrrolidone, tetramethylene sulphone or dimethylsulphoxide, and preferably with the exclusion of moisture or water.

The polyether ketones thus accessible can have molecular weights of 20,000 and more, for example in the range of from 20'000 to 45'000'and are distinguished by a high stability to changes in temperature. These polyether ketones are useful as fillers for such polymers which are to be used for the manufacture of temperature resistant mouldings. They can also be used as intermediates for preparing pharmaceuticals and biocides.

The examples which follow illustrate the present invention, without in any way restricting it.

EXAMPLES

EXAMPLE 1

200 ml of hydrogen fluoride were introduced into a stainless steel reactor at 0° C. and 146 g of benzotrifluoride and 30 g of trioxane were added in succession. The mixture was stirred at 20° C. for 6 hours. Thereafter, the hydrogen fluoride was distilled off, first under normal pressure and then in vacuo. The residue which remained was then subjected to fractional distillation. After unreacted benzotrifluoride had initially passed over, 96 g of 3,3'-bis-trifluoromethyl-diphenylmethane with a boiling point of 130° to 140° C. under 22 mbar and a melting point of 39°–40° C. were obtained.

EXAMPLE 2

The procedure followed was as in Example 1, but 30 g of polymeric formaldehyde were employed instead of trioxane. 66 g of 3,3'-bis-trifluoromethyl-diphenylmethane were obtained.

EXAMPLE 3

180 g of 4-chlorobenzotrifluoride and 39 g of paraformaldehyde were taken at 20° C. and stirred for 1 hour. 100 g of fluorosulphonic acid were then added dropwise in the course of 2 hours. After the reaction mixture had been stirred at 20° C. for 10 hours, it was poured onto ice and the organic phase which formed was separated off. Fractional distillation initially gave unreacted 4-chlorobenzotrifluoride, followed by 67 g of 2,2'-dichloro-5,5'-bistrifluoromethyl-diphenylmethane with a boiling point of 168° to 173° C. under 20 mbar at a melting point of 32° to 34° C.

EXAMPLE 4

The procedure followed was as in Example 3, but 60 g of paraformaldehyde were employed and 105 g of 2,2'-dichloro-5,5'-bistrifluoromethyl-diphenylmethane were obtained.

EXAMPLE 5

90 g of 2-chloro-5-methyl-benzotrifluoride and 30 g of paraformaldehyde were introduced into a stainless steel reactor and 100 ml of fluorosulphonic acid were added dropwise at 20° C. After the reaction mixture had been stirred at 20° C. for 5 hours, it was poured onto ice and the solid products present were filtered off with suction and recrystallised from cyclohexane. 42 g of 2,2'-dichloro-3,3'-bistrifluoromethyl-5,5'-dimethyl-diphenylmethane of melting point 118° to 120° C. were obtained.

EXAMPLE 6

180 g of 2-chlorobenzotrifluoride, 50 g of paraformaldehyde and 250 g of fluorosulphonic acid were reacted by a procedure analogous to that described in Example 5. Distillation gave 145 g of 4,4'-dichloro-3,3'-bistrifluoromethyl-diphenylmethane of boiling point 185° to 190° C./20 mbar and melting point 102° to 104° C., from methanol.

EXAMPLE 7

900 g of 2-chloro-benzotrifluoride and 250 g of paraformaldehyde were introduced into a stainless steel stirred apparatus at 10° C. At this temperature, 700 g of fluorosulphonic acid were then added dropwise and the mixture was stirred for a further 15 hours. After the mixture had been discharged onto 2,000 g of ice, the organic material was taken up in methylene chloride and the organic phase was washed with water, dried and subjected to fractional distillation. Besides methylene chloride, 186 g of unreacted 2-chlorobenzotrifluoride were initially recovered. 659 g of 4,4'-dichloro-3,3'-benzotrifluoromethyl-diphenylmethane of boiling point 180° to 188° C. under 16 mbar were then obtained.

EXAMPLE 8

84 g of urotropine, 300 ml of hydrogen fluoride and 97 g of trifluoromethoxybenzene were heated at 80° C. in a stainless steel autoclave for 5 hours. After the hydrogen fluoride had been distilled off, the residue was poured onto water, the mixture was stirred for 30 minutes and then extracted with methylene chloride and the dried organic phase was then subjected to fractional distillation. 11 g of 4,4'-bistrifluoromethoxy-diphenylmethane of boiling point 141° to 143° C. under 18 mbar were obtained.

EXAMPLE 9

160 g of 2-methylbenzotrifluoride, 140 g of urotropine and 500 ml of hydrogen fluoride were reacted by a procedure corresponding to that described in Example 8. 45 g of 3,3'-bistrifluoromethyl-4,4-dimethyldiphenylmethane of melting point 86°–87° C. and boiling point 135° to 140° C. under 0.15 mbar were obtained.

EXAMPLE 10

The procedure followed was as in Example 9, but 30 g of paraformaldehyde were employed instead of urotropine and the reaction was carried out at 20° C. 133 g of 4,4'-dimethyl-3,3'-bistrifluoromethyl-diphenylmethane of melting point 88° C. (recrystallized from methanol) were obtained.

EXAMPLE 11

360 g of 4-chlorobenzotrifluoride and 150 g of paraformaldehyde were introduced into a polyethylene reaction vessel at 20° C. and 200 ml of fluorosulphonic acid were added dropwise at 20° C., with stirring. Thereafter, stirring was continued for 10 hours, 500 g of ice were then introduced and the organic phase was dissolved in methylene chloride. After the organic phase had been separated off, it was dried and then subjected to fractional distillation. 108 g of unreacted 4-chlorobenzotrifluoride were obtained, followed by intermediate runnings of 23 g, and then 200 g of 2,2'-dichloro-5,5'-bis-trifluoromethyl-diphenylmethane of boiling point 130° to 140° C. under 0.45 mbar, and a residue of 24 g, which predominantly consisted of products of a higher degree of condensation.

EXAMPLE 12

390 g of bis-(4-chloro-3-trifluoromethyl-phenyl)-methane obtained according to Example 7 were added to 2,000 ml of 65% strength by weight nitric acid and the mixture was heated at the boiling point under reflux for 12 hours. After cooling, the solid product present was filtered off with suction (408 g) and recrystallised from methanol. The resulting 4,4'-dichloro-3,3'-bistrifluoromethyl-benzophenone had a melting point of 98° to 101° C.

EXAMPLE 13

100 ml of sulphuric acid were added to a mixture consisting of 60 g of sodium dichromate and 500 ml of acetic acid. 30 g of bis-(2-chloro-5-trifluoromethylphenyl)-methane, obtained according to Example 3, were then added dropwise at 45° C. The reaction mixture was subsequently stirred at 45° to 50° C. for 3 hours and then cooled and poured into water. After the mixture had been extracted with methylene chloride and the solvent had been stripped off, 22 g of 2,2'-dichloro-5,5'-bistrifluoromethyl-benzophenone of melting point 70° to 72° C. were obtained.

EXAMPLE 14

54 g of 4,4'-difluoro-3,3'-bistrifluoromethyl-benzophenone of melting point 83° to 84° C. were obtained from 60 g of bis-(4-fluoro-3-trifluoromethyl-phenyl)-methane by a procedure corresponding to that described in Example 12.

EXAMPLE 15

A mixture of 50 g of 2-chloro-2,3,3-trifluorobenzodioxene, 20 g of trioxane and 100 ml of hydrogen fluoride was heated at 60° C. in an autoclave for 5 hours, hydrogen fluoride and unreacted starting substance were then stripped off in vacuo and the residue which remained was distilled. 29 g of bis-(2-chloro-2,3,3-trifluorobenzodioxenyl)-methane of boiling point 150° to 155° C. under 0.1 mbar and refractive index $n_D^2 = 1.5098$ were obtained.

EXAMPLE 16

12 g of hydroquinone were reacted with 2.5 g of sodium hydride in 300 ml of dry N-methyl-pyrrolidone and, when the salt formation had ended, 36 g of 4,4'-difluoro-3,3'-bistrifluoromethyl-benzophenone were added. The mixture was then heated at 150° C. for 15 hours, with exclusion of moisture. After cooling, the solvent was distilled off in vacuo and the residue was washed thoroughly with water and then dried. A polymer of polyether ketone type with side chains containing fluorine, a melting range from 250° to 255° C. and a molecular weight of more than 20,000 was obtained. The polymer was distinguished by a high stability to changes in temperature.

What is claimed is:

1. A symmetric benzophenone substituted by a flourine containing group of the formula

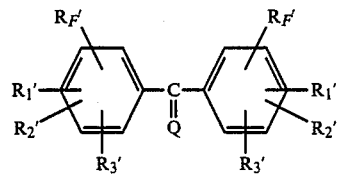

in which $R_F'$ represents $CF_3$ in the 3- and 3'-position, $R_1'$ represents hydrogen, $R_2'$ represents hydrogen, and $R_3'$ represents halogen.

2. A compound according to claim 1, wherein the halogen is selected from the group consisting of flourine and chlorine.

* * * * *

UNITED STATES PATENT AND TRADEMARK OFFICE
CERTIFICATE OF CORRECTION

PATENT NO. : 4,792,635
DATED : December 20, 1988
INVENTOR(S) : Albrecht Marhold, et al It is certified that error appears in the above-identified patent and that said Letters Patent is hereby corrected as shown below:

| | |
|---|---|
| Col. 2, line 36 | Delete "($R_F$" and substitute --$R_F$-- |
| Col. 5, lines 36 and 47 | Delete "RF" and substitute --$R_F$-- |
| Col. 5, line 53 | Correct spelling of --dihydroxy-diphenyl-- |
| Col. 5, line 65 | Delete "20'000 to 45'000'" and substitute --20,000 to 45,000,-- |
| Col. 8, line 33 | Delete "$n_D{}^2$" and substitute --$n_D{}^{20}$-- |
| Col. 8, line 58 | Delete "$-\overset{\|}{\underset{O}{C}}-$" and substitute -- $-\overset{\|}{\underset{O}{C}}-$ -- |
| Col. 8, line 66 | Delete "flourine" and substitute --fluorine-- |

Signed and Sealed this

Seventeenth Day of October, 1989

*Attest:*

DONALD J. QUIGG

*Attesting Officer*  *Commissioner of Patents and Trademarks*